(12) United States Patent
Gallant et al.

(10) Patent No.: US 12,402,979 B2
(45) Date of Patent: Sep. 2, 2025

(54) SURGICAL FIDUCIAL MARKER POSITIONER

(71) Applicant: Medivis, Inc., New York, NY (US)

(72) Inventors: Jesse Harrison Gallant, New York, NY (US); Christopher Morley, New York, NY (US); Osamah Choudhry, New York, NY (US)

(73) Assignee: Medivis, Inc., New York, NY (US)

( * ) Notice: Subject to any disclaimer, the term of this patent is extended or adjusted under 35 U.S.C. 154(b) by 25 days.

(21) Appl. No.: 18/135,674

(22) Filed: Apr. 17, 2023

(65) Prior Publication Data

US 2024/0341907 A1    Oct. 17, 2024

(51) Int. Cl.
*A61B 90/00*    (2016.01)

(52) U.S. Cl.
CPC ...... *A61B 90/39* (2016.02); *A61B 2090/3916* (2016.02); *A61B 2090/3979* (2016.02); *A61B 2090/3991* (2016.02)

(58) Field of Classification Search
None
See application file for complete search history.

(56) References Cited

U.S. PATENT DOCUMENTS

| | | | | |
|---|---|---|---|---|
| 6,366,799 B1* | 4/2002 | Acker | ..................... | A61B 5/064 |
| | | | | 600/424 |
| 2004/0167391 A1* | 8/2004 | Solar | ...................... | A61B 90/39 |
| | | | | 600/426 |
| 2015/0182293 A1* | 7/2015 | Yang | ................... | A61B 17/1703 |
| | | | | 600/424 |
| 2017/0105802 A1* | 4/2017 | Taraschi | ................. | A61B 34/20 |
| 2020/0188034 A1* | 6/2020 | Lequette | ................ | A61B 90/39 |
| 2022/0142730 A1* | 5/2022 | Wolf | ..................... | A61B 90/361 |
| 2022/0184824 A1* | 6/2022 | Collet | ...................... | B25J 5/007 |
| 2022/0265365 A1* | 8/2022 | Redmond | .............. | A61B 34/20 |
| 2023/0172668 A1* | 6/2023 | Collet | .................. | A61F 2/4607 |
| | | | | 606/130 |

FOREIGN PATENT DOCUMENTS

EP        3470040 B1 *  3/2022  ......... A61B 17/1675

* cited by examiner

*Primary Examiner* — Jeffrey G Hoekstra
*Assistant Examiner* — Ashish S Jasani
(74) *Attorney, Agent, or Firm* — Cognition IP, P.C.; Edward Steakley; Justin White (57) ABSTRACT

A surgical fiducial marker positioner can include a rigid frame and a positioner coupling component. The rigid frame can support a plurality of surgical fiducial markers at fixed positions relative to each other along the rigid frame to form a fixed positional arrangement of surgical fiducial markers. The rigid frame can define a polygon arranged along a plane and the fixed positional arrangement of surgical fiducial markers can be asymmetrical. The positioner coupling component can be coupled to the rigid frame and can be configured to couple the surgical fiducial marker positioner to a separate surgical component at fixed position(s) relative to the separate surgical component, which can be a spinous process clamp. The surgical fiducial marker positioner can also include the surgical fiducial markers and fiducial marker couplers that removably couple the surgical fiducial markers to the rigid frame at the fixed positions.

20 Claims, 10 Drawing Sheets

SURGICAL FIDUCIAL MARKER POSITIONER

CROSS-REFERENCE TO RELATED APPLICATION

This application is related to commonly owned U.S. patent application Ser. No. 18/135,663 filed on this same date of Apr. 17, 2023 and entitled "SPINOUS PROCESS CLAMP," which application is hereby incorporated by reference in its entirety herein.

TECHNICAL FIELD

The present disclosure relates generally to medical devices, and more particularly to surgical tools and devices used during medical surgeries and procedures.

BACKGROUND

Planning and navigation are necessary for many medical procedures, and surgical teams typically have a plan based on medical imagery before ever entering an operating room. Conventional medical imaging systems such as X-ray, MRI, CT, and others have limitations regarding two-dimensional and three-dimensional images, however, and surgeons often need to consider numerous image views and slices to plan surgical procedures. Recent medical advances leverage these applications of medical imagery and surgical plans by using a computer-aided augmented reality environment, which can allow for the tracking of patients and physical instruments during surgical procedures by using fiducial markers and tracking components.

Unfortunately, conventional tracking systems are often limited in their ability to accurately generate, render, and apply virtual interactions in an augmented reality environment based on the orientations and positions of physical instruments with respect to those of physical landmarks identified on a patient body, particularly when things move during surgery. Unstable or unreliable positioning of fiducial markers can play a role in these issues. Limited or inaccurate tracking can then affect the overall performance of such systems during surgical procedures.

While traditional ways of virtually tracking items during surgery have worked well in the past, improvements are always helpful. In particular, what is desired are medical systems and devices that facilitate the stable and reliable positioning of fiducial markers during surgery.

SUMMARY

It is an advantage of the present disclosure to provide medical systems and devices that facilitate the stable and reliable positioning of fiducial markers during surgery in a simple and streamlined manner. The disclosed features, apparatuses, systems, and methods relate to positioners that can be used to locate fiducial markers and other devices during surgeries and other medical procedures. In particular, the disclosed systems and methods can involve surgical fiducial marker positioners that can reliably locate fiducial markers relative to a patient and that can be coupled to one or more other surgical devices or items, such as a spinous process clamp.

In various embodiments of the present disclosure, a surgical fiducial marker positioner can include at least a rigid frame and a positioner coupling component. The rigid frame can be configured to support a plurality of surgical fiducial markers at fixed positions relative to each other along the rigid frame to form a fixed positional arrangement of surgical fiducial markers. The rigid frame can define a polygon arranged along a plane and the fixed positional arrangement of surgical fiducial markers can be asymmetrical. The positioner coupling component can be coupled to the rigid frame and can be configured to couple the surgical fiducial marker positioner to a separate surgical component at a first fixed position relative to the separate surgical component.

In various detailed embodiments, the surgical fiducial marker positioner can include the plurality of surgical fiducial markers, which can be infrared reflective spheres, retroreflective spheres, infrared-emitting diodes, or any other suitable form of fiducial marker. The surgical fiducial marker positioner can also include a plurality of fiducial marker couplers, each of which can removably couple one of the plurality of surgical fiducial markers to the rigid frame at one of the fixed positions. The rigid frame can include marker openings therein that removably couple the marker couplers at each of the fixed positions. In some arrangements, the plurality of surgical fiducial markers can include six or more surgical fiducial markers. Also, the polygon defined by the rigid frame can be a hexagon, which can be regularly or irregularly shaped. The rigid frame can include a plurality of arm segments arranged to form the polygon. Each of the plurality of arm segments can include at least one of the fixed positions configured to support one of the plurality of surgical fiducial markers.

In further detailed embodiments, the separate surgical component can be a spinous process clamp configured to grip a spinous process of a patient. The positioner coupling component can be configured to couple the surgical fiducial marker positioner to the spinous process clamp or other separate surgical component at a second fixed position relative to the separate surgical component that is different than the first fixed position. In some arrangements, the positioner coupling component can be configured to rotationally couple the surgical fiducial marker positioner to the separate surgical component at multiple fixed rotational positions relative to the separate surgical component. Also, the positioner coupling component can be configured to allow rotation of the surgical fiducial marker positioner relative to the separate surgical component without uncoupling from the separate surgical component.

In further embodiments of the present disclosure, various methods of using a surgical fiducial marker positioner are provided. Pertinent process steps can include at least loosening a coupling, adjusting an orientation of the surgical fiducial marker positioner, and tightening the coupling. The coupling can be between the surgical fiducial marker positioner and a separate surgical component. The orientation can be relative to the separate surgical component, and adjusting the orientation can be from a first fixed position to a second fixed position. The tightened coupling can prevent further relative movements between the surgical fiducial marker positioner and the separate surgical component.

In various detailed embodiments, the separate surgical component can be a spinous process clamp configured to grip a spinous process of a patient. The coupling can be a rotational coupling and the orientation can be a rotational orientation. In addition, the surgical fiducial marker positioner can include a rigid frame and a positioner coupling component as set forth above, as well as any further details and variations thereof. Further process steps of the disclosed methods can include removably coupling a plurality of surgical fiducial markers to the surgical fiducial marker positioner at fixed positions relative to each other to form an asymmetrical fixed positional arrangement of surgical fiducial markers, forming the coupling between the surgical fiducial marker positioner and the separate surgical component, wherein the separate surgical component is a spinous process clamp, the coupling is a rotational coupling, the orientation is a rotational orientation, and the first and second fixed positions are rotational fixed positions, and confirming that the spinous process clamp firmly grips a spinous process of a patient and that the asymmetrical fixed positional arrangement of surgical fiducial markers is usable by a separate surgical system when the surgical fiducial marker positioner is at the second rotational fixed position.

In various further embodiments of the present disclosure, a surgical fiducial marker system can include a clamp and a surgical fiducial marker positioner. The clamp can be configured to grip a fixed item during a medical procedure regarding a patient, and the fixed item can be the patient or an item relative to the patient. The surgical fiducial marker positioner can be movably coupled to the clamp and can be configured to position a plurality of surgical fiducial markers into a fixed arrangement relative to the patient while the clamp grips the fixed item. The surgical fiducial marker positioner can include a rigid frame configured to support a plurality of surgical fiducial markers at fixed positions relative to each other along the rigid frame to form a fixed positional arrangement of surgical fiducial markers, wherein the rigid frame defines a polygon arranged along a plane and the fixed positional arrangement of surgical fiducial markers is asymmetrical. The positioner coupling component can be coupled to the rigid frame, can be configured to rotationally couple the surgical fiducial marker positioner to the clamp, and can be further configured to facilitate at least ten different discrete rotational positions of the surgical fiducial marker positioner with respect to the clamp.

Other apparatuses, methods, features, and advantages of the disclosure will be or will become apparent to one with skill in the art upon examination of the following figures and detailed description. It is intended that all such additional apparatuses, methods, features and advantages be included within this description, be within the scope of the disclosure, and be protected by the accompanying claims.

BRIEF DESCRIPTION OF THE DRAWINGS

The included drawings are for illustrative purposes and serve only to provide examples of possible structures, arrangements, and methods of use for surgical fiducial marker positioners. These drawings in no way limit any changes in form and detail that may be made to the disclosure by one skilled in the art without departing from the spirit and scope of the disclosure.

DETAILED DESCRIPTION

Exemplary applications of apparatuses, systems, and methods according to the present disclosure are described in this section. These examples are being provided solely to add context and aid in the understanding of the disclosure. It will thus be apparent to one skilled in the art that the present disclosure may be practiced without some or all of these specific details provided herein. In some instances, well known process steps have not been described in detail in order to avoid unnecessarily obscuring the present disclosure. Other applications are possible, such that the following examples should not be taken as limiting. In the following detailed description, references are made to the accompanying drawings, which form a part of the description and in which are shown, by way of illustration, specific embodiments of the present disclosure. Although these embodiments are described in sufficient detail to enable one skilled in the art to practice the disclosure, it is understood that these examples are not limiting, such that other embodiments may be used, and changes may be made without departing from the spirit and scope of the disclosure.

As is generally well known, modern surgical plans and procedures are sometimes facilitated by using a computer-aided augmented reality environment. Surgical fiducial markers can be used for tracking of patients and physical instruments during surgical procedures in overall systems that can also include specialized lighting arrangements, cameras, and computing systems. Attachment devices are often used to affix the surgical fiducial markers in place relative to the patient, and unstable or unreliable positioning of these markers can result in the reduced effectiveness of the overall computer-aided augmented reality environment. The disclosed surgical attachment devices are specifically designed to facilitate the stable and reliable positioning of fiducial markers during surgery in a simple and streamlined manner.

The present disclosure relates in various embodiments to features, apparatuses, systems, and methods of use for surgical positioning devices, and in particular surgical fiducial marker positioners. This can generally involve positioners or other suitable locating devices that are configured to facilitate the stable and reliable positioning of fiducial markers during surgery in a simple and streamlined manner. In specific arrangements, this can involve surgical fiducial marker positioners that can reliably locate fiducial markers relative to a patient and that can be coupled to one or more other surgical devices or items, such as a spinous process clamp.

In various embodiments of the present disclosure, novel surgical fiducial marker positioners can include at least a rigid frame or other suitable structure and a positioner coupling component coupled thereto. The rigid frame can support a plurality of surgical fiducial markers at fixed positions relative to each other along the rigid frame to form a fixed positional arrangement of surgical fiducial markers that is asymmetrical. The surgical fiducial markers and/or marker couplers that removably couple the surgical fiducial markers to the frame can also be part of a surgical fiducial marker positioner. The positioner coupling component can couple the surgical fiducial marker positioner to a separate surgical component at a first fixed position relative to the separate surgical component, which can be a spinous process clamp.

Although various embodiments disclosed herein discuss the use of a surgical fiducial marker positioner in conjunction with a spinous process clamp as part of an overall surgical fiducial marker system, it will be readily appreciated that the disclosed features, apparatuses, systems, and methods can also be used in conjunction with other devices and equipment that can leverage the advantages of a fiducial marker positioner. While the disclosed surgical fiducial marker positioners are contemplated for uses involving coupling to spinous process clamps that then clamp to spinous processes during a surgical procedure, it is specifically contemplated that other coupled objects and clamped targets and applications may also be applied. For example, the disclosed surgical fiducial marker positioners can couple to other body parts or other fixed items for surgical and non-surgical uses, such as during examination and testing procedures. Other devices and equipment that can be coupled to the disclosed surgical fiducial marker positioners can include alternative clamps and fixation components, which can clamp or affix the disclosed positioners to other body parts, lighting arrangements, sensing devices, or other desired equipment. Other applications, arrangements, and extrapolations beyond the illustrated embodiments are also contemplated.

Figure 1A:
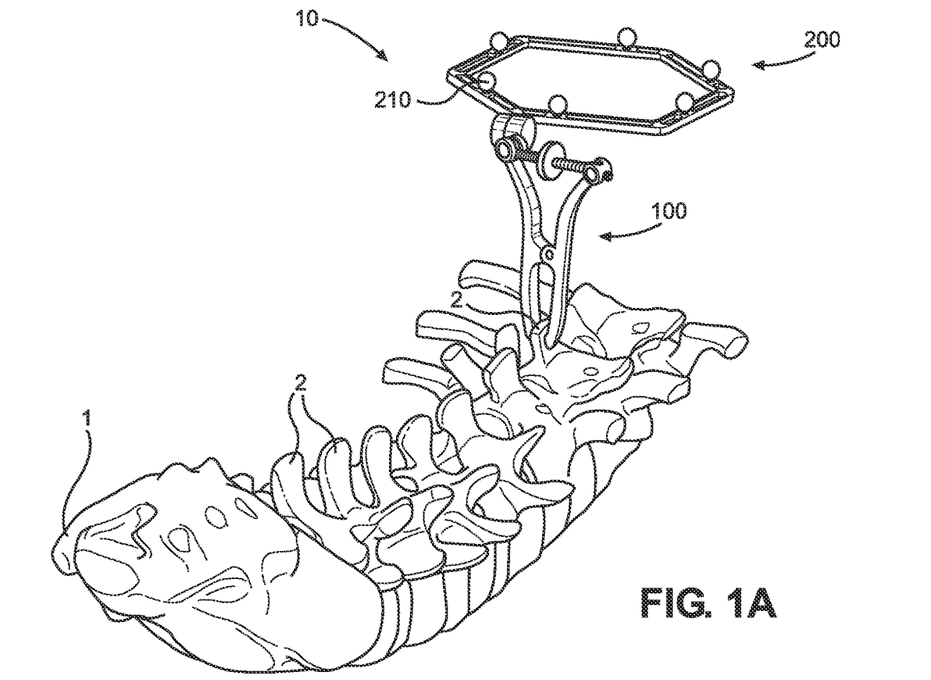
FIG. 1A illustrates in front perspective view an example surgical fiducial marker system having a surgical fiducial marker positioner and spinous process clamp coupled to a patient spine according to one embodiment of the present disclosure.
Figure 1B:
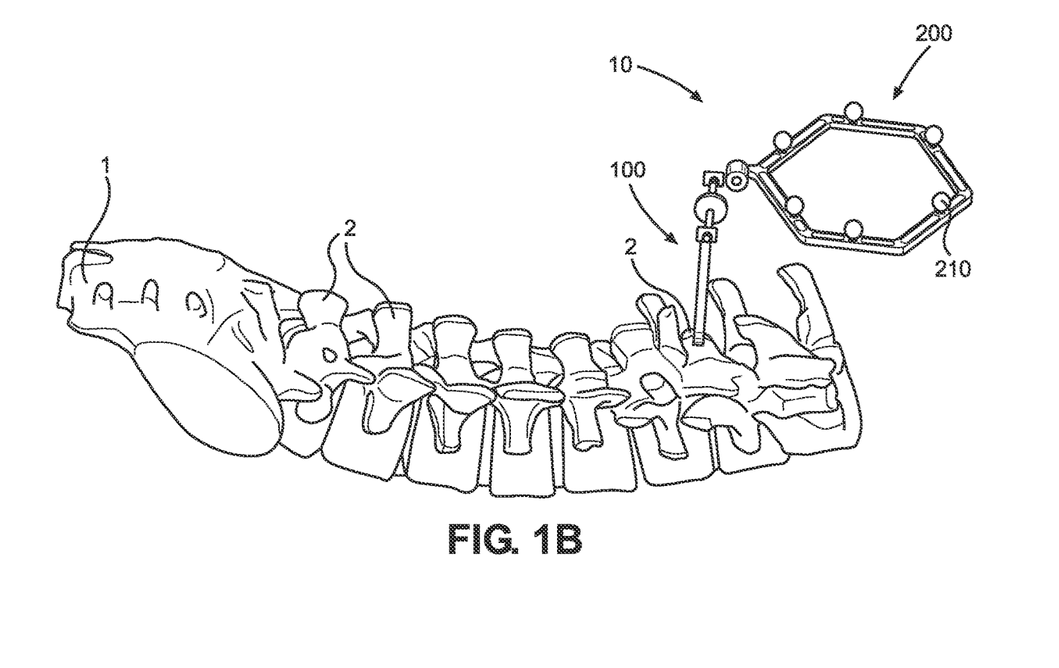
FIG. 1B illustrates in side perspective view the surgical fiducial marker system of FIG. 1A coupled to the patient spine according to one embodiment of the present disclosure.

Referring first to FIGS. 1A and 1B, an example surgical fiducial marker system having a surgical fiducial marker positioner and spinous process clamp coupled to a patient spine is illustrated in front perspective and side perspective views respectively. Surgical fiducial marker system 10 can generally include a spinous process clamp 100 and a surgical fiducial marker positioner 200. Spinous process clamp 100 can be clamped to one of various spinous processes 2 along the spine 1 of a patient. Surgical fiducial marker positioner 200 can be coupled to spinous process clamp 100 and can be configured to position multiple surgical fiducial markers 210 with respect to the patent spine 1. As shown, spinous process clamp 100 can be firmly clamped to a spinous process and set at a fixed position relative to the patient and surgical fiducial marker positioner 200 can be firmly coupled to the spinous process clamp and set at a fixed position relative thereto, such that the surgical fiducial markers 210 are set at a fixed arrangement relative to the patient.

Figure 2A:
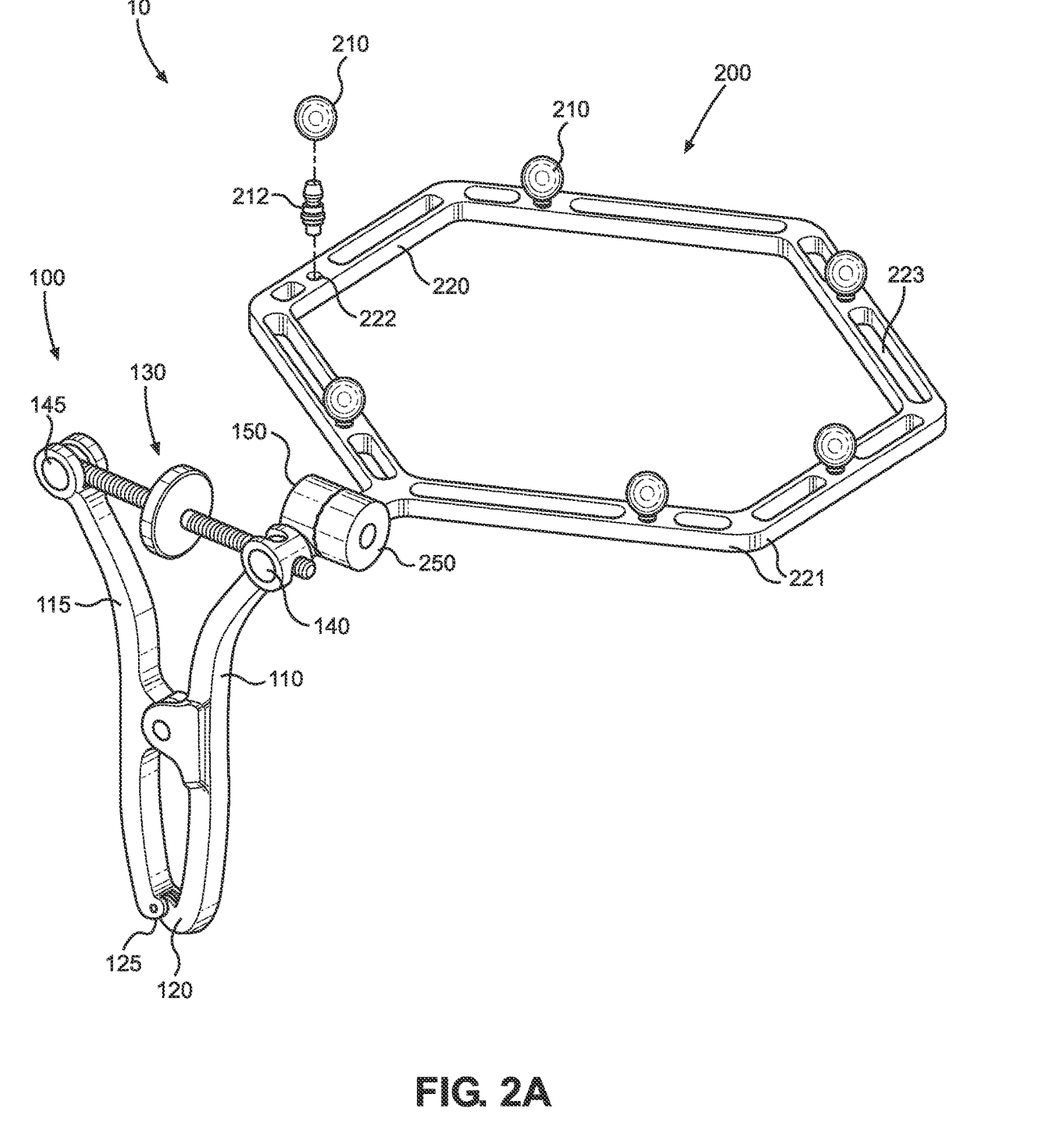
FIG. 2A illustrates in front perspective view an example surgical fiducial marker system having a surgical fiducial marker positioner rotationally coupled to a spinous process clamp according to one embodiment of the present disclosure.
Figure 2B:
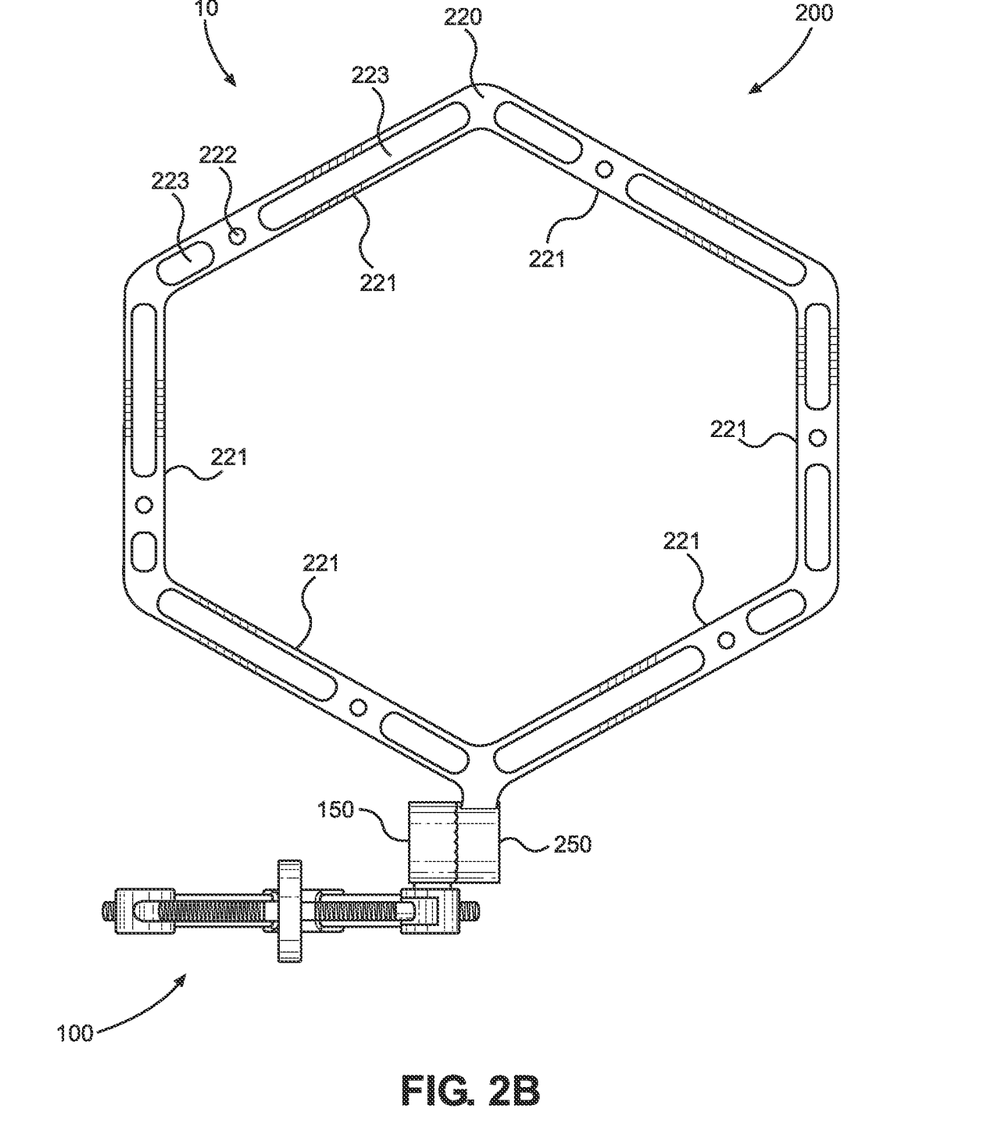
FIG. 2B illustrates in top plan view the surgical fiducial marker system of FIG. 2A with the surgical fiducial marker positioner oriented perpendicular to the spinous process clamp according to one embodiment of the present disclosure.

Continuing with FIGS. 2A and 2B, an example surgical fiducial marker system having a surgical fiducial marker positioner rotationally coupled to and oriented perpendicular to a spinous process clamp is shown in front perspective and top plan views respectively. Again, surgical fiducial marker system 10 can generally include a spinous process clamp 100 and a surgical fiducial marker positioner 200. Surgical fiducial marker positioner 200 can be coupled to spinous process clamp 100 by way of positioner coupling component 250 that can be configured to interact with clamp coupling component 150 of the clamp, as detailed below. In some embodiments, surgical fiducial marker positioner 200 can include surgical fiducial markers 210 coupled to a rigid frame 220 of multiple arm segments 221 by way of fiducial marker couplers 212 that insert into marker openings 222 in an asymmetrical fixed positional arrangement, among various other components and features as set forth in greater detail below.

In various embodiments, spinous process clamp 100 can include a first arm 110, a second arm 115, a first gripping component 120, a second gripping component 125, an adjustable spacing arrangement 130 including a first receiving bearing 140 and a second receiving bearing 145, and a clamp coupling component 150, among other possible components and features. While clamp coupling component 150 is shown as being located proximate the top of first arm 110, it will be readily appreciated that this coupling component can alternatively be located at various other places on spinous process clamp 100, such as proximate the top of second arm 115 for example. Further details regarding spinous process clamp 100 and variations thereof can be found in related U.S. patent application Ser. No. 18/135,663 entitled "SPINOUS PROCESS CLAMP," which application is again hereby incorporated by reference in its entirety.

As shown in FIG. 2B, the surgical fiducial markers and fiducial marker couplers can be removed from marker openings 222 in rigid frame 220, such that surgical fiducial marker positioner 200 can be a standalone device without these items in some arrangements. The same or new surgical fiducial markers and fiducial marker couplers can then be removably coupled to rigid frame 220. In various embodiments, surgical fiducial markers 210 can include infrared reflective spheres or balls, other retroreflective spheres, infrared-emitting diodes, or other items suitable for use with surgical optical tracking systems. Each surgical fiducial marker 210 can be coupled to an arm segment 221 along rigid frame 220 of surgical fiducial marker positioner 200 using a threaded coupler 212 that can be inserted into an opening of the fiducial marker as well as a marker opening 222 along the arm segment 221. Some or all of multiple arm segments 221 can have one or more marker openings 222 as well as one or more structural openings 223 therethrough, such as where it is desirable for the overall surgical fiducial marker positioner 200 to be lightweight and the remaining material has sufficient structural strength. All arm segments 221 and positioner coupling component 250 can be integrally formed into a single unit that can be comprised of medical grade plastic and/or stainless steel, among other possible arrangements and suitable materials.

The multiple arm segments 221 of surgical fiducial marker positioner 200 can be arranged into a rigid frame 220 arranged along a plane and having a polygon shape, such as six arm segments combining to form a hexagon, for example. Such a polygon shape can be irregular in some arrangements or may be symmetrical. The locations of marker openings 222 can form an asymmetrical pattern such that installation of surgical fiducial markers into all of the marker openings then results in a fixed positional arrangement of surgical fiducial markers that is asymmetrical such that it that will not cause ambiguity or confusion with the optical tracking system reading the locations of the fiducial markers. Although each arm segment 221 is shown as having a single marker opening 222 in FIG. 2B, it will be readily appreciated that each arm segment can have zero or multiple marker openings. In any such arrangement, it is contemplated that installing surgical fiducial markers into all or any subset of all marker openings 222 can still result in a fixed positional arrangement of surgical fiducial markers that is still asymmetrical.

Figure 3A:
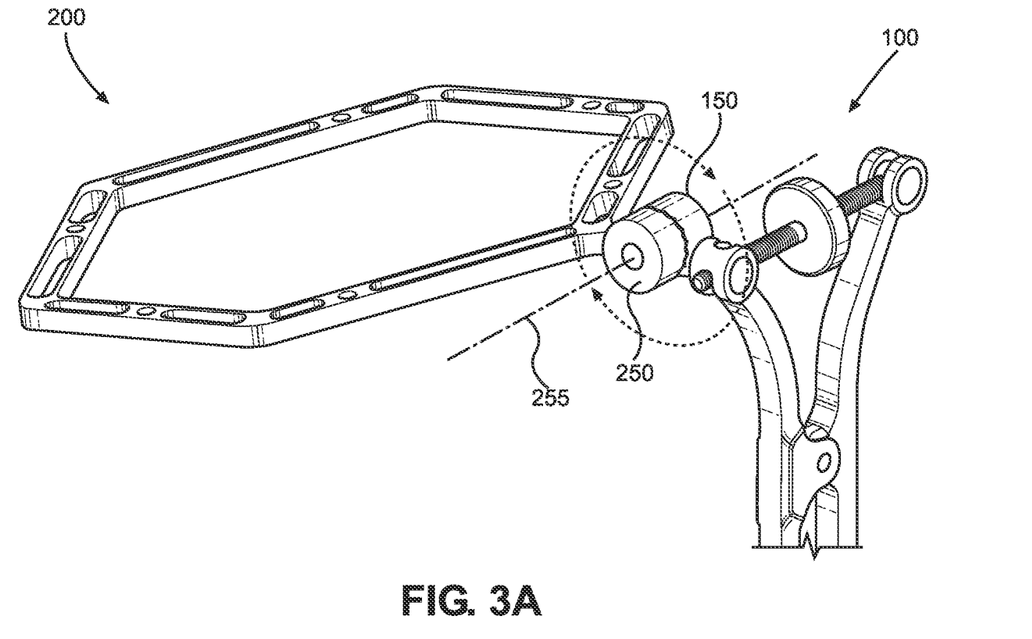
FIG. 3A illustrates in side perspective view an example surgical fiducial marker positioner at a first fixed rotational position relative to a coupled spinous process clamp according to one embodiment of the present disclosure.
Figure 3B:
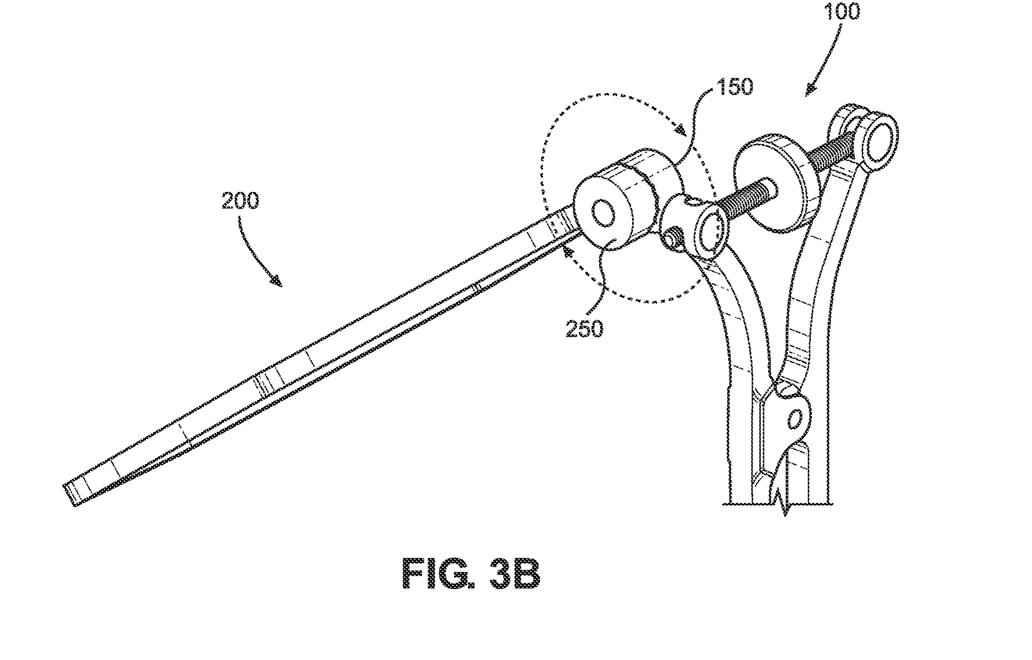
FIG. 3B illustrates in side perspective view the surgical fiducial marker positioner of FIG. 3A at a second fixed rotational position relative to the coupled spinous process clamp according to one embodiment of the present disclosure.

Focusing now on FIGS. 3A and 3B, an example surgical fiducial marker positioner is shown in side perspective views at first and second fixed rotational positions relative to a coupled spinous process clamp. In various arrangements, positioner coupling component 250 can be rotationally coupled to and configured to rotate with respect to clamp coupling component 150, which can be affixed to and stationary with respect to spinous process clamp 100. Rotation can be about a horizontal axis 255 that extends through the centers of positioner coupling component 250 and clamp coupling component 150, such that the position of entire surgical fiducial marker positioner 200 can be rotated about this axis. Changeable and different rotational positions may be desirable for a variety of reasons, such as to provide better visibility or usage of surgical fiducial markers to a separate surgical optical tracking system and/or to facilitate the structural stability and balance of overall surgical fiducial marker system 10, for example.

While the rotational orientation of surgical fiducial marker positioner 200 relative to spinous process clamp 100 is shown to be about perpendicular (i.e., 90 degrees) in FIGS. 2A-2B, this rotational orientation can be at many different angles. For example, a first fixed rotational position of surgical fiducial marker positioner 200 is shown to be slightly less than perpendicular or 90 degrees in FIG. 3A, and a second fixed rotational position is shown to be about 45 degrees in FIG. 3B. Such fixed rotational positions can extend between 0 and 180 degrees and even beyond in various arrangements. A discrete number of fixed rotational positions can be achieved in some arrangements by way of mating features of positioner coupling component 250 and clamp coupling component 150, as set forth in greater detail below.

Figure 4:
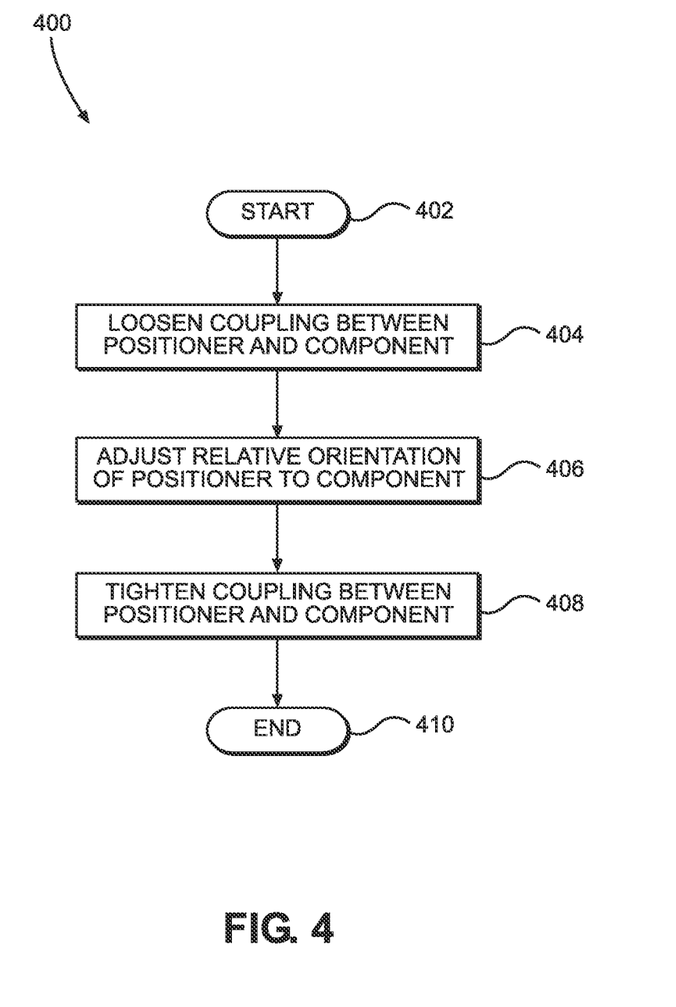
FIG. 4 illustrates a flowchart of an example summary method of using a surgical fiducial marker positioner according to one embodiment of the present disclosure.

Moving next to FIG. 4, a flowchart of an example summary method of using a surgical fiducial marker positioner is provided. Summary method 400 can represent one broad aspect of various overall methods of use for a surgical fiducial marker positioner, and it will be understood that other steps, features, and details of such a broad aspect and overall methods of use are not provided here for purposes of simplicity. After a start step 402, a first process step 404 can involve loosening a coupling between the surgical fiducial marker positioner and a separate surgical component, which can be a spinous process clamp as one possible example. This can involve loosening a thumbscrew, wing nut, or other coupling arrangement between a positioner coupling component and a corresponding coupling component of the clamp or other separate surgical component, for example. Also, this can take place when the coupling arrangement is already tightened with the surgical fiducial marker positioner being at a first fixed position relative to the separate surgical component. Step 404 can be manually or automatically performed, such as where a separate robotic system can be configured to adjust the positioning of the surgical fiducial marker positioner.

At a following process step 406, an orientation of the surgical fiducial marker positioner relative to the separate surgical component can be adjusted from a first fixed position to a second fixed position. This can involve moving the surgical fiducial marker positioner while the separate surgical component remains stationary, for example, such as by rotation about an axis through a positioner coupling component and a corresponding coupling component that remain loosely coupled, among other possible relative movements. Step 406 can be manually or automatically performed, such as where a separate robotic system can be configured to adjust the positioning of the surgical fiducial marker positioner.

The next process step 408 can involve tightening the coupling between the surgical fiducial marker positioner and the separate surgical component. This can be done when the surgical fiducial marker positioner is at the second fixed position, for example, and the tightened coupling can prevent further relative movements between the surgical fiducial marker positioner and the separate surgical component. Step 408 can be manually or automatically performed, such as where a separate robotic system can be configured to adjust the positioning of the surgical fiducial marker positioner. The method can then end at end step 410.

Figure 5A:
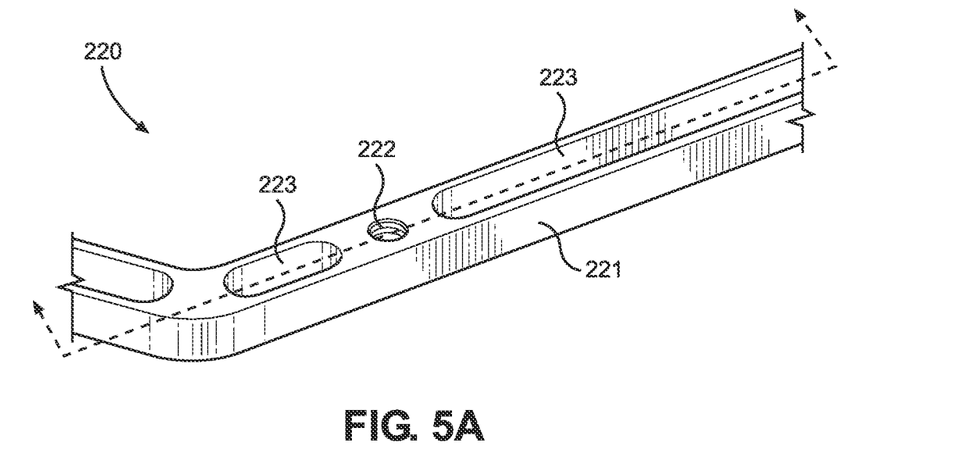
FIG. 5A illustrates in top perspective view an example arm segment of a surgical fiducial marker positioner according to one embodiment of the present disclosure.
Figure 5B:
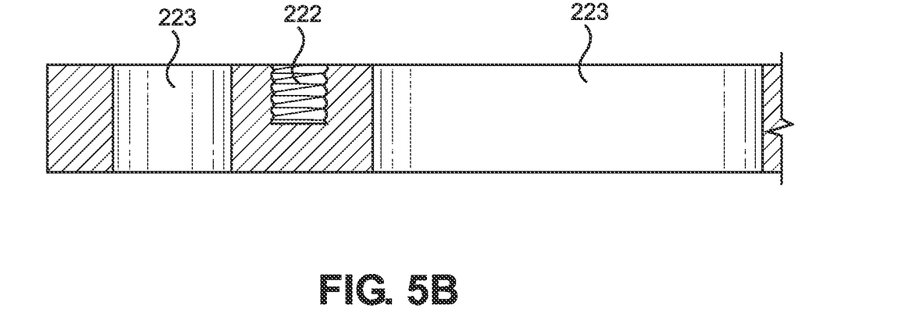
FIG. 5B illustrates in side cross section view the arm segment of FIG. 5A according to one embodiment of the present disclosure.

Transitioning now to FIGS. 5A and 5B, an example arm segment of a surgical fiducial marker positioner is shown in top perspective and side cross-section views respectively. As noted above, a surgical fiducial marker positioner can include a rigid frame 220 that includes multiple arm segments 221 arranged into a polygon shape, such as by forming or otherwise coupling all of the arm segments end to end to form the frame. Again, each arm segment 221 can have one or more marker openings 222 and one or more structural openings 223 extending into its material from a top surface thereof. Some or all of these marker openings 222 and structural openings 223 can extend all the way through arm segment 221.

Figure 5C:
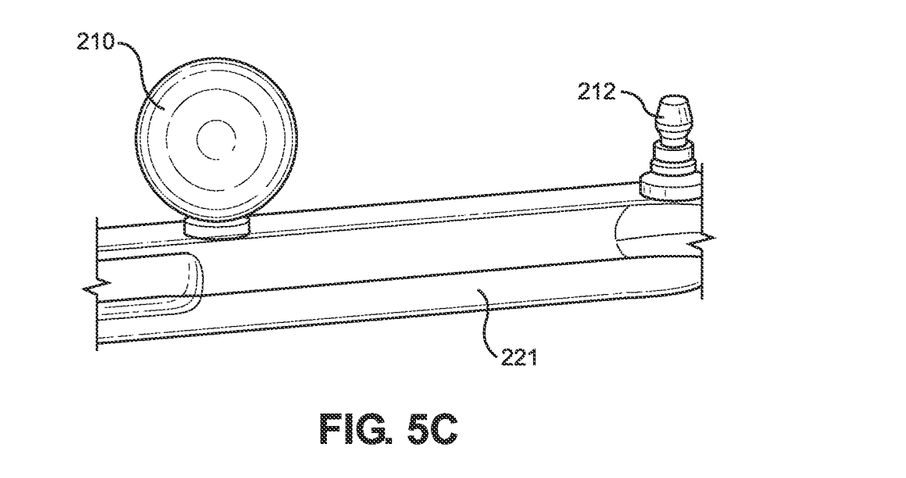
FIG. 5C illustrates in side perspective view an example alternative surgical fiducial marker positioner arm segment with a fiducial marker and fiducial marker coupler coupled thereto according to one embodiment of the present disclosure.

FIG. 5C illustrates in side perspective view an example alternative surgical fiducial marker positioner arm segment with a fiducial marker and fiducial marker coupler coupled thereto. This arm segment 221 can include multiple fiducial marker couplers 212 that insert into marker openings along a top surface of the arm segment such that surgical fiducial markers 210 can be fitted onto the fiducial marker couplers, such as by way of holes or openings in the surgical fiducial markers. In some arrangements, all of these fittings or couplings between arm segment 221 and fiducial marker couplers 212, and also the fiducial marker couplers and surgical fiducial markers 210 can be removable such that the fiducial markers can be removed and reinstalled or replaced, as will be readily understood by those of skill in the art.

Figure 6A:
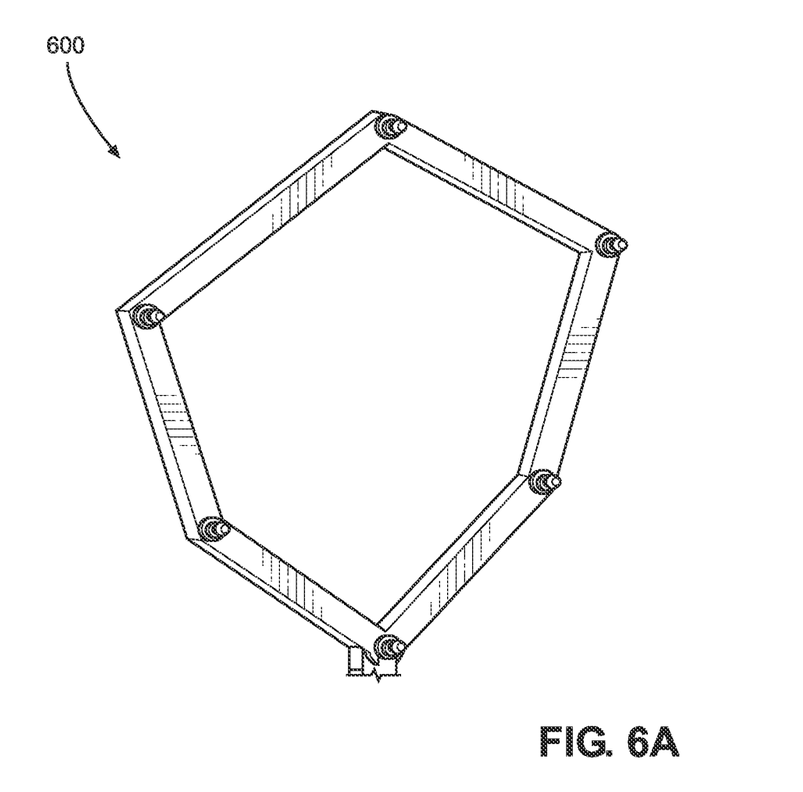
FIG. 6A illustrates in top plan view an example alternative surgical fiducial marker positioner according to one embodiment of the present disclosure.
Figure 6B:
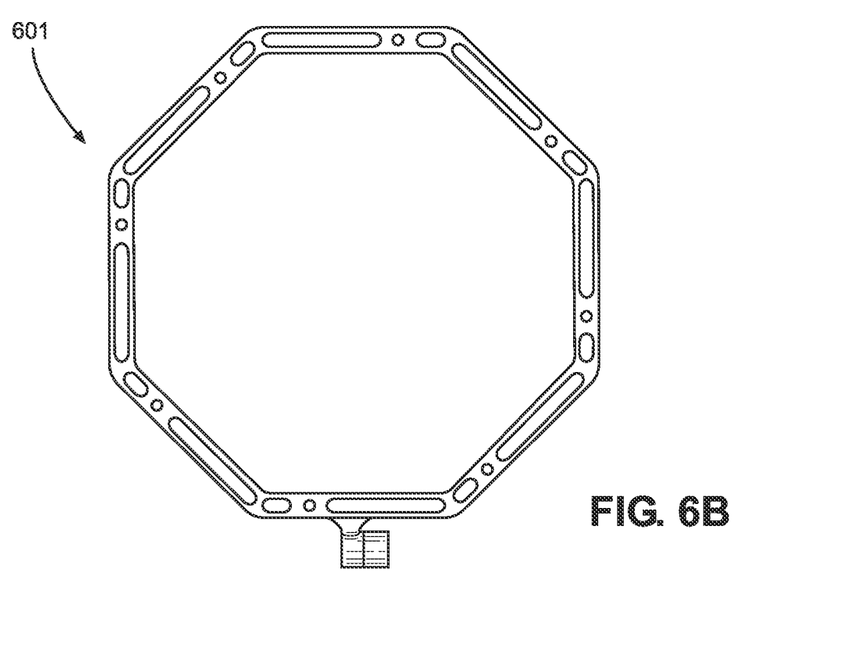
FIG. 6B illustrates in top plan view an example further alternative surgical fiducial marker positioner according to one embodiment of the present disclosure.

Moving next to FIGS. 6A and 6B, various alternative surgical fiducial marker positioners are depicted in top plan view. Surgical fiducial marker positioner 600 can have an alternative frame arrangement arranged along a plane and having an irregular hexagonal shape, for example. Also, fiducial marker couplers can be located at joints or intersections between arm segments as shown rather than along the arm segments. Although six surgical fiducial markers and six arm segments arranged into a hexagon shape have been shown for purposes of illustration for surgical fiducial marker positioners 200 and 600, it will be understood that a suitable surgical fiducial marker positioner may also have more or fewer fiducial markers arranged along more or fewer arm segments arranged into other shapes. Such other shapes can include rectangles, pentagons, octagons, for example, among other possible shapes. As another non-limiting illustrative example, surgical fiducial marker positioner 601 can have a rigid frame arranged along a plane into an octagon shape with eight fixed locations for fiducial marker couplers and fiducial markers. Other arrangements can include frames having seven arm segments arranged into an irregular shape, and other shapes and amounts of arm segments are also possible, as will be readily appreciated.

Figure 7A:
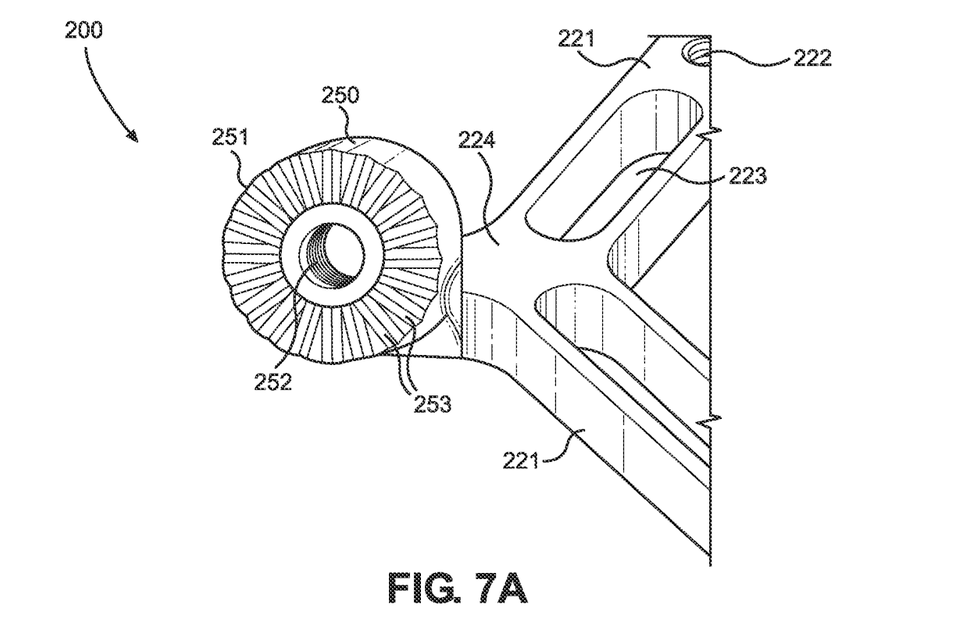
FIG. 7A illustrates in perspective view an example positioner coupling component for a surgical fiducial marker positioner according to one embodiment of the present disclosure.
Figure 7B:
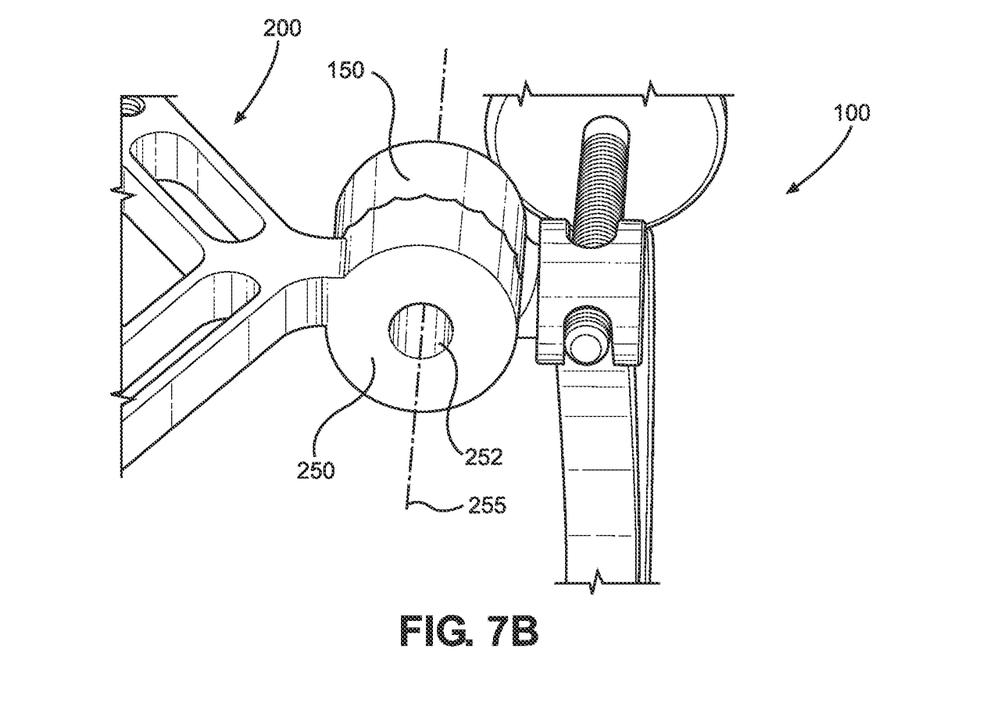
FIG. 7B illustrates in perspective view the positioner coupling component of FIG. 7A rotationally coupled to a clamp coupling component for a spinous process clamp according to one embodiment of the present disclosure.

Continuing with FIGS. 7A and 7B, an example positioner coupling component for a surgical fiducial marker positioner is illustrated in perspective views both alone and also as being rotationally coupled to a clamp coupling component for a spinous process clamp. Again, surgical fiducial marker positioner 200 can include multiple arm segments 221 having marker openings 222 and optional structural openings 223. A neck 224 can extend from one of arm segments 221 or a junction between arm segments for attaching or coupling positioner coupling component 250. In some arrangements, neck 224 and positioner coupling component 250 can be integrally formed with the rigid frame having arm segments 221.

Positioner coupling component 250 can define a cylindrical shape having a vertically oriented circular mating face 251 and a threaded central opening 252 extending at least partially therethrough. Mating face 251 can have a plurality of ridges 253 that can be arranged in an axial pattern for mating with a similar axial pattern of ridges on a mating face of clamp coupling component 150. In addition to having a corresponding mating face that is configured to mate and operate with mating face 251, clamp coupling component 150 can similarly have a threaded central opening arranged to align with the threaded central opening 252 of positioner coupling component 250 when both mating faces are engaged.

In various arrangements, clamp coupling component 150 can be affixed to and can be stationary with spinous process clamp 100, while positioner coupling component 250 can be affixed to surgical fiducial marker positioner 200 and configured to rotate the entire surgical fiducial marker positioner with respect to the clamp coupling component. Rotation can be about a horizontal axis 255 that extends through the centers of threaded central opening 252 and the corresponding threaded central opening of clamp coupling component 150, such that the position of entire surgical fiducial marker positioner 200 is rotated about this axis. As will be readily appreciated, rotation of positioner coupling component 250 with respect to stationary clamp coupling component 150 can result in the relative rotation of its mating face 251 with a corresponding mating face of the clamp coupling component.

Ridges 253 on mating face 251 can fit snugly between corresponding ridges on the mating face of clamp coupling component 150, such that multiple discrete rotational orientations can be achieved. For example, where positioner coupling component 250 has a mating face 251 with ten axially arranged ridges 253, then clamp coupling component 150 can have a matching mating face with ten similarly axially arranged ridges, and this can facilitate at least ten different discrete rotational positions of surgical fiducial marker positioner 200 with respect to the spinous process clamp 100. Of course, more or fewer axially arranged ridges are also possible, and positioner coupling component 250 as shown can have twenty such axially arranged ridges 253 for twenty different discrete rotational positions in this particular illustrative example. In some embodiments, a thumbscrew, wing nut, or other coupling arrangement (not shown) can be used within threaded internal opening 252 and corresponding threaded internal opening of clamp coupling component 150 to loosen and tighten positioner coupling component 250 with respect to clamp coupling component 150. As will be readily appreciated, loosening such a coupling arrangement can allow for the ready rotational adjustment of surgical fiducial marker positioner 200 with respect to spinous process clamp 100, while tightening such a coupling arrangement can result in affixing or setting a discrete rotational position of the surgical fiducial marker positioner with respect to the spinous process clamp or other separate surgical component. One possible coupling arrangement between positioner coupling component 250 and clamp coupling component 150 can involve a thumbscrew and threaded post that can insert into threaded internal opening 252, details of which are shown in related U.S. patent application Ser. No. 18/135,663 entitled "SPINOUS PROCESS CLAMP," which application is again hereby incorporated by reference in its entirety. Of course, other suitable coupling arrangements are also possible.

While clamp coupling component 150 and positioner coupling component 250 are shown as being vertically oriented with respect to spinous process clamp 100 in FIGS. 7A-B and other illustrative examples herein, it will be readily appreciated that these coupling components can be oriented horizontally or otherwise, such that relative rotation can be about a differently oriented axis. It is also contemplated that more than one rotational axis can be used for adjusting the positioning of surgical fiducial marker positioner 200 in some embodiments. For example, a secondary mating coupling component arrangement can allow for rotation of the surgical fiducial marker positioner 200 with respect to the spinous process clamp 100 about a vertical axis as well as a horizontal axis.

Figure 8A:
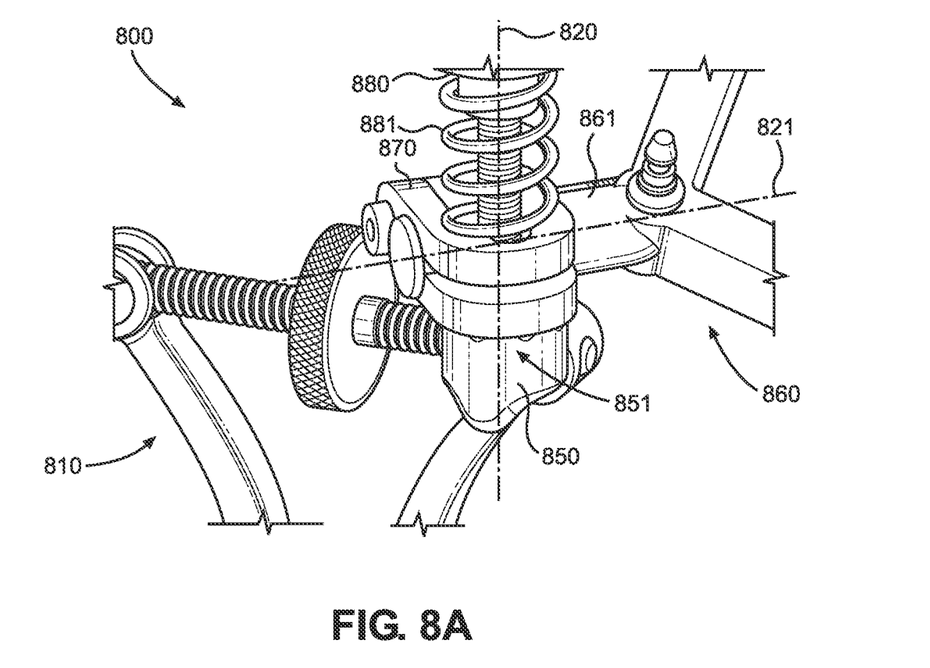
FIG. 8A illustrates in perspective view an example alternative positioner coupling component for a surgical fiducial marker positioner according to one embodiment of the present disclosure.
Figure 8B:
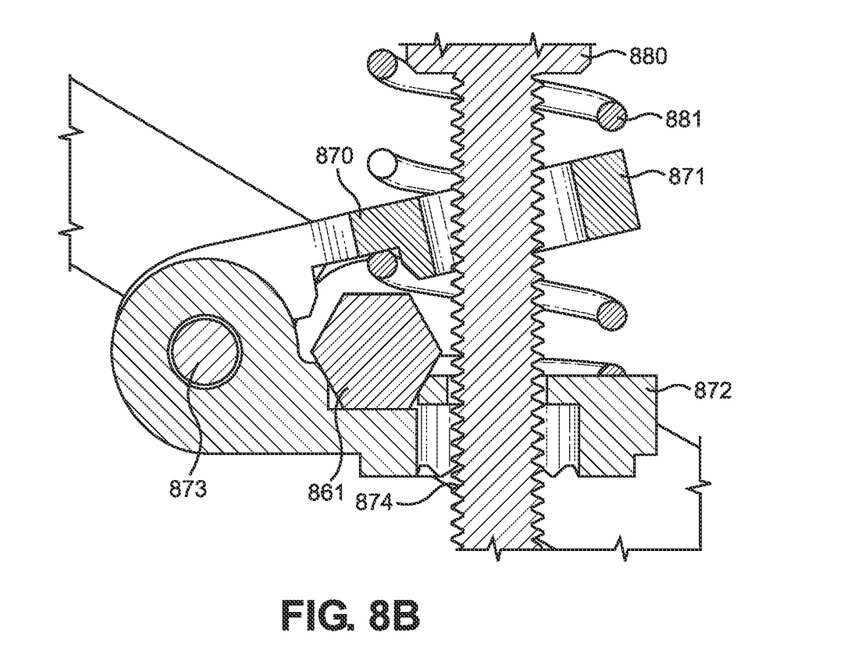
FIG. 8B illustrates in perspective view the alternative positioner coupling component of FIG. 8A rotationally coupled to a clamp coupling component for a spinous process clamp according to one embodiment of the present disclosure.

FIGS. 8A and 8B illustrate an example alternative coupling arrangement between a surgical fiducial marker positioner and spinous process clamp in perspective and cross-section views respectively. Alternative surgical fiducial marker system 800 can generally include spinous process clamp 810 and surgical fiducial marker positioner 860, both of which can be substantially similar in many respects and details to spinous process clamp 100 and surgical fiducial marker positioner 200 above. Unlike surgical fiducial marker system 10 disclosed in detail above, however, alternative surgical fiducial marker system 800 can have a coupling arrangement that facilitates relative rotation about multiple axes, such as vertical axis 820 and horizontal axis 821. Spinous process clamp 810 can have an alternative clamp coupling component 850 while surgical fiducial marker positioner 860 can have an alternative positioner coupling component 870 or arrangement to facilitate this alternative coupling arrangement.

As shown, clamp coupling component 850 can be coupled to or located proximate a top distal end of an arm of spinous process clamp 810, while positioner coupling component 870 can be rotationally coupled around a neck 861 extending from surgical marker positioner 860. A mating face 851 at a top surface of clamp coupling component 850 can have axial ridges and be configured to mate with a similar mating face 874 along a bottom surface of positioner coupling component 870. Such a rotational mating arrangement can be similar to the rotational mating arrangement set forth above between clamp coupling component 150 and positioner coupling component 250, except with mating faces 851, 874 facilitating a horizontal rotation of fiducial marker positioner 860 relative to stationary spinous process clamp 810 about vertical axis 820.

To facilitate an axial rotation of fiducial marker positioner 860 relative to stationary spinous process clamp 810 about horizontal axis 821, a portion of neck 861 can extend into and can be configured to rotate within positioner coupling component 870. This can be facilitated by positioner coupling component 870 having a top portion 871 and a bottom portion 872 that are hinged or coupled about a pivot pin 873 such these top and bottom portions can clamp onto and release off from neck 861. As shown, at least a portion of neck 861 inside of positioner coupling component 870 can have a discrete polygonal cross-section shape to facilitate discrete rotational amounts and positions of the neck. Thumbscrew 880 and bias spring 881 can facilitate the ability to loosen and tighten the fit of positioner coupling component 870 around neck 861, as well as to loosen and tighten the fit of mating faces 851 and 874, as will be readily appreciated by those of skill in the art. Although this alternative coupling arrangement of alternative surgical fiducial marker system 800 having multiple axes of relative rotation has been provided for purposes of illustration, it will be understood that other types of coupling arrangements between a surgical fiducial marker positioner and a clamp or other separate surgical component can also be used, and that such other types of coupling arrangements can have more or few axes or rotation, other ways of loosening and tightening coupling components, and even other forms of relative movement or positioning besides rotational movement.

Figure 9:
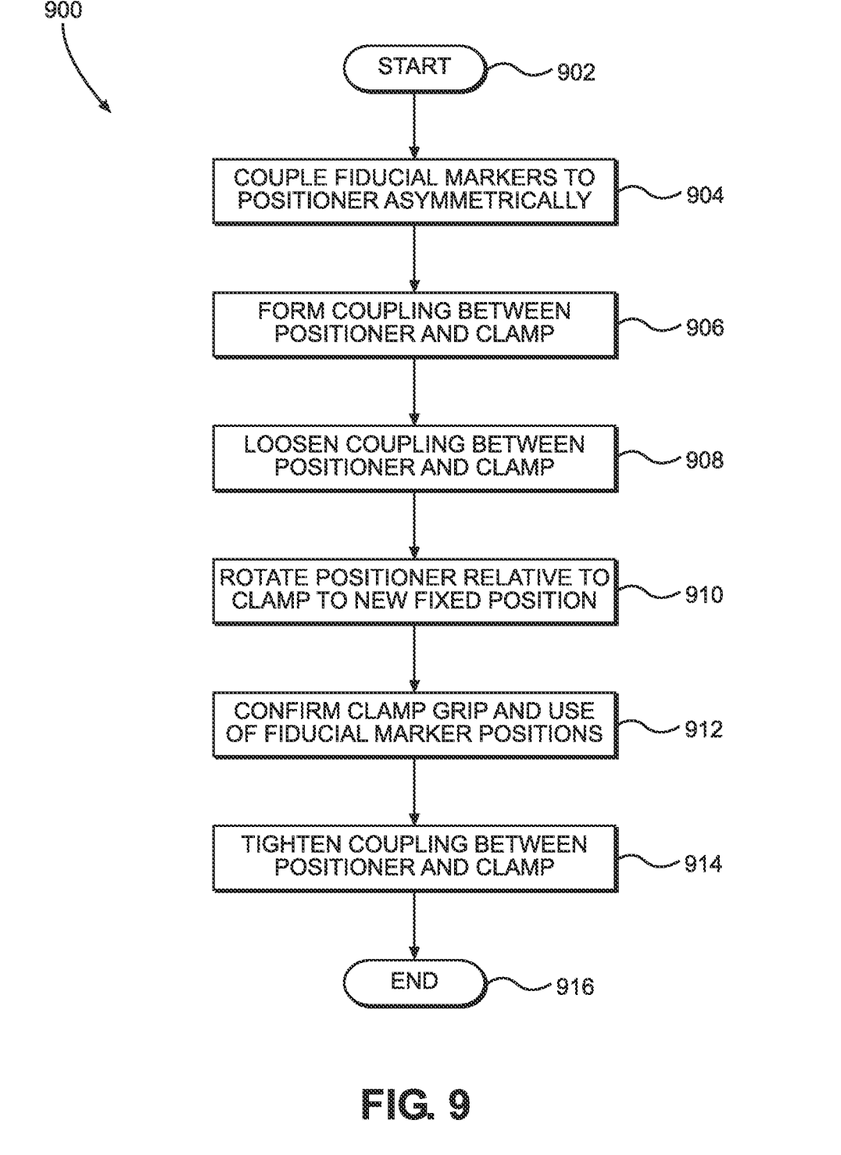
FIG. 9 illustrates a flowchart of an example detailed method of using a surgical fiducial marker positioner according to one embodiment of the present disclosure.

Lastly, FIG. 9 provides a flowchart of an example detailed method 900 of using a surgical fiducial marker positioner. Detailed method 900 can represent one possible way of using a surgical fiducial marker positioner, and it will be understood that various other steps, features, and details of such a detailed method are not provided here for purposes of simplicity. After a start step 902, a first process step 904 can involve coupling surgical fiducial markers to a surgical fiducial marker positioner. This can involve removably coupling the surgical fiducial markers to the surgical fiducial marker positioner at fixed positions relative to each other to form an asymmetrical fixed positional arrangement of surgical fiducial markers, and can also include the use of fiducial marker couplers that removably couple to both the fiducial markers and the surgical fiducial marker positioner. Step 904 can be manually or automatically performed, such as where a separate robotic system can be configured to couple the surgical fiducial markers to the surgical fiducial marker positioner.

At the next process step 906, a coupling can be formed between the surgical fiducial marker positioner and a separate surgical component, such as a spinous process clamp. This can be a rotational coupling involving threaded openings in mating components, a threaded bar, and one or more thumbscrews, wing nuts, or other suitable tighteners, for example. Step 906 can be manually or automatically performed, such as where a separate robotic system can be configured to couple a surgical fiducial marker positioner to a spinous process clamp or another separate surgical component.

A following process step 908 can involve loosening the coupling between the surgical fiducial marker positioner and spinous process clamp or other separate surgical component. This can involve loosening a thumbscrew, wing nut, or other coupling arrangement between a positioner coupling component and a corresponding coupling component of the clamp or other separate surgical component. This can take place when the coupling arrangement is already tightened with the surgical fiducial marker positioner being at a first fixed position relative to the separate surgical component, or alternatively this step can be skipped if the formed coupling is already loose such that rotational adjustments are possible. Step 908 can be manually or automatically performed, such as where a separate robotic system can be configured to adjust the positioning of the surgical fiducial marker positioner.

At a subsequent process step 910, the surgical fiducial marker positioner can be rotated relative to the clamp or other separate surgical component to a new fixed position. This can involve rotating the surgical fiducial marker positioner while the clamp or other separate surgical component remains stationary, such as by rotation about an axis through a positioner coupling component and a corresponding coupling component that remain loosely coupled. Rotation can be from a first fixed position to a second fixed position, for example. Step 910 can be manually or automatically performed, such as where a separate robotic system can be configured to adjust the positioning of the surgical fiducial marker positioner.

The next process step 912 can involve confirming that the spinous process clamp firmly grips a spinous process of a patient and also that the asymmetrical fixed positional arrangement of surgical fiducial markers is usable by a separate surgical system when the surgical fiducial marker positioner is at the second rotational fixed position. Step 912 can be manually or automatically performed, such as where a separate robotic system can be configured to register the visibility and positions of all surgical fiducial markers and that none of these fiducial markers are moving or otherwise unstable when the overall system is set.

At the following process step 914, the coupling can be tightened between the surgical fiducial marker positioner and the clamp or other separate surgical component. This can be done when the surgical fiducial marker positioner is at the second fixed position, for example, and the tightened coupling can prevent further relative movements between the surgical fiducial marker positioner and the clamp or other separate surgical component. Step 914 can be manually or automatically performed, such as where a separate robotic system can be configured to adjust the positioning of the surgical fiducial marker positioner. The method can then end at end step 916.

For foregoing method 900, it will be appreciated that not all process steps are necessary, and that other process steps may be added in some arrangements. For example, removing old fiducial markers and cleaning or sterilizing the surgical fiducial marker positioner might take place before coupling new fiducial markers may take place in some arrangements. Other steps may involve functions of the associated spinous process clamp or other separate surgical component. Furthermore, the order of steps may be altered in some cases, and some steps may be performed simultaneously. For example, step 912 may be performed after step 914 in some cases. Although known process steps are provided for the various techniques in method 900, it will be appreciated that any other suitable similar method for using a surgical fiducial marker positioner can also be used. Other variations and extrapolations of the disclosed methods will also be readily appreciated by those of skill in the art.

Although the foregoing disclosure has been described in detail by way of illustration and example for purposes of clarity and understanding, it will be recognized that the above described disclosure may be embodied in numerous other specific variations and embodiments without departing from the spirit or essential characteristics of the disclosure. Certain changes and modifications may be practiced, and it is understood that the disclosure is not to be limited by the foregoing details, but rather is to be defined by the scope of the appended claims.

What is claimed is:

1. A surgical fiducial marker positioner, comprising:
   a rigid frame configured to support a plurality of surgical fiducial markers at fixed positions relative to each other along the rigid frame to form a fixed positional arrangement of surgical fiducial markers, wherein the rigid frame includes a plurality of arm segments within a plane and arranged in the shape of a polygon, wherein each of the plurality of arm segments includes at least one of the fixed positions configured to support one of the plurality of surgical fiducial markers, and wherein the fixed positional arrangement of surgical fiducial markers is asymmetrical; and
   a positioner coupling component coupled to the rigid frame, wherein the positioner coupling component is configured to couple the surgical fiducial marker positioner to a separate surgical component at a first fixed position relative to the separate surgical component.

2. The surgical fiducial marker positioner of claim 1, further comprising:
   the plurality of surgical fiducial markers.

3. The surgical fiducial marker positioner of claim 2, wherein the surgical fiducial markers include infrared reflective spheres, retroreflective spheres, or infrared-emitting diodes.

4. The surgical fiducial marker positioner of claim 2, further comprising:
   a plurality of fiducial marker couplers, wherein each fiducial marker coupler removably couples one of the plurality of surgical fiducial markers to the rigid frame at one of the fixed positions.

5. The surgical fiducial marker positioner of claim 4, wherein the rigid frame includes marker openings therein that removably couple the marker couplers at each of the fixed positions.

6. The surgical fiducial marker positioner of claim 2, wherein the plurality of surgical fiducial markers includes six or more surgical fiducial markers.

7. The surgical fiducial marker positioner of claim 1, wherein the polygon defined by the rigid frame is a hexagon.

8. The surgical fiducial marker positioner of claim 1, wherein the separate surgical component is a spinous process clamp configured to grip a spinous process of a patient.

9. The surgical fiducial marker positioner of claim 1, wherein the positioner coupling component is configured to couple the surgical fiducial marker positioner to the separate surgical component at a second fixed position relative to the separate surgical component that is different than the first fixed position.

10. The surgical fiducial marker positioner of claim 1, wherein the positioner coupling component is configured to rotationally couple the surgical fiducial marker positioner to the separate surgical component at multiple fixed rotational positions relative to the separate surgical component.

11. The surgical fiducial marker positioner of claim 10, wherein the positioner coupling component is configured to allow rotation of the surgical fiducial marker positioner relative to the separate surgical component without uncoupling from the separate surgical component.

12. The surgical fiducial marker positioner of claim 1, wherein the rigid frame includes an open center and the plurality of arm segments are arranged around and enclose the open center to form the polygon.

13. The surgical fiducial marker positioner of claim 1, wherein each of the plurality of arm segments includes at least one structural opening therethrough at a location separate from any fixed position configured to support one of the plurality of surgical fiducial markers.

14. The surgical fiducial marker positioner of claim 1, wherein each of the plurality of arm segments and the positioner coupling component are all integrally formed from the same material.

15. The surgical fiducial marker positioner of claim 1, wherein the positioner coupling component is coupled to the rigid frame by way of a neck extending from one or more of the plurality of arm segments.

16. The surgical fiducial marker positioner of claim 1, wherein the positioner coupling component is configured to rotationally couple the surgical fiducial marker positioner to the separate surgical component such that the rigid frame is rotatable about a first axis extending through the positioner coupling component and is further configured to facilitate multiple discrete fixed rotational positions of the surgical fiducial marker positioner with respect to the separate surgical component with the multiple discrete fixed rotational positions extending over a range that exceeds 180 degrees.

17. The surgical fiducial marker positioner of claim 1, wherein the positioner coupling component is configured to provide a removable coupling to the separate surgical component, is configured to provide a loosened coupling to the separate surgical component such that the surgical fiducial marker positioner can be rotated relative to the separate surgical component while coupled, and is configured to provide a tightened coupling to the separate surgical component such that the surgical fiducial marker positioner cannot be rotated relative to the separate surgical component.

18. A surgical fiducial marker system, comprising:
   a clamp configured to grip a fixed item during a medical procedure regarding a patient, wherein the fixed item is the patient or an item relative to the patient; and
   a surgical fiducial marker positioner movably coupled to the clamp, wherein the surgical fiducial marker positioner is configured to position a plurality of surgical fiducial markers into a fixed arrangement relative to the patient while the clamp grips the fixed item, and wherein the surgical fiducial marker positioner includes:
- a rigid frame configured to support a plurality of surgical fiducial markers at fixed positions relative to each other along the rigid frame to form a fixed positional arrangement of surgical fiducial markers, wherein the rigid frame includes a plurality of arm segments within a plane and arranged in the shape of a polygon and each of the plurality of arm segments includes at least one of the fixed positions configured to support one of the plurality of surgical fiducial markers, wherein the fixed positional arrangement of surgical fiducial markers is asymmetrical, and
- a positioner coupling component coupled to the rigid frame, wherein the positioner coupling component is configured to rotationally couple the surgical fiducial marker positioner to the clamp such that the rigid frame is rotatable about a first axis extending through the positioner coupling component and is further configured to facilitate multiple discrete fixed rotational positions of the surgical fiducial marker positioner with respect to the clamp with the multiple discrete fixed rotational positions extending over a range that exceeds 180 degrees.

19. The surgical fiducial marker system of claim 18, wherein the positioner coupling component is configured to rotationally couple the surgical fiducial marker positioner to the clamp such that the rigid frame is also rotatable about a second axis extending through the positioner coupling component, the second axis being orthogonal to the first axis.

20. The surgical fiducial marker system of claim 18, wherein the positioner coupling component is configured to provide a removable coupling to the clamp, is configured to provide a loosened coupling to the clamp such that the surgical fiducial marker positioner can be rotated relative to the clamp while coupled, and is configured to provide a tightened coupling to the clamp such that the surgical fiducial marker positioner cannot be rotated relative to the clamp.

* * * * *